United States Patent [19]
Franceschi et al.

[11] Patent Number: 4,956,373
[45] Date of Patent: Sep. 11, 1990

[54] PHARMACEUTICAL COMPOSITION COMPRISING 3-(N-PIPERIDINOMETHYL-AZINO) METHYLRIFAMYCIN S AS ACTIVE INGREDIENT

[75] Inventors: Giovanni Franceschi; Sergio Vioglio, both of Milan; Roberto Bianchini, Bergamo, all of Italy

[73] Assignee: Farmitalia Carlo Erba S.R.L, Milan, Italy

[21] Appl. No.: 353,472

[22] Filed: May 18, 1989

Related U.S. Application Data

[63] Continuation-in-part of Ser. No. 304,033, Jan. 31, 1989, abandoned.

[51] Int. Cl.$^5$ ............................................ A61K 31/445
[52] U.S. Cl. .................................................. 514/321
[58] Field of Search ................................. 514/183, 321

[56] References Cited

U.S. PATENT DOCUMENTS 4,447,432  5/1984  Franceschi et al. ................ 514/183

Primary Examiner—Jerome D. Goldberg
Attorney, Agent, or Firm—Oblon, Spivak, McClelland, Maier & Neustadt

[57] ABSTRACT

Orally administrable pharmaceutical compositions comprising 3-(N-piperidinomethyl-azino)methylrifamycin S as the active substance are disclosed. The active substance is easily soluble in water even at low pH values and is provided with good bioavailability. Such compositions are useful in the treatment of bacterial infections.

1 Claim, No Drawings

PHARMACEUTICAL COMPOSITION COMPRISING 3-(N-PIPERIDINOMETHYL-AZINO) METHYLRIFAMYCIN S AS ACTIVE INGREDIENT

BACKGROUND OF THE INVENTION

This is a continuation-in-part of U.S. patent application Ser. No. 07/304,033 filed Jan. 31, 1989.

Field of the Invention

The present invention relates to a pharmaceutical composition comprising 3-(N-piperidinomethylazino)-methylrifamycin S as the active ingredient.

DISCUSSION OF THE BACKGROUND

U.S. Pat. No. 4,447,432 and the corresponding U.K. Pat. No. 2,110,677 and Japanese LOP 92682/83 (application No. 199147/82), all in the name of the present applicants, disclose and claim azino-rifamycin compounds of formula

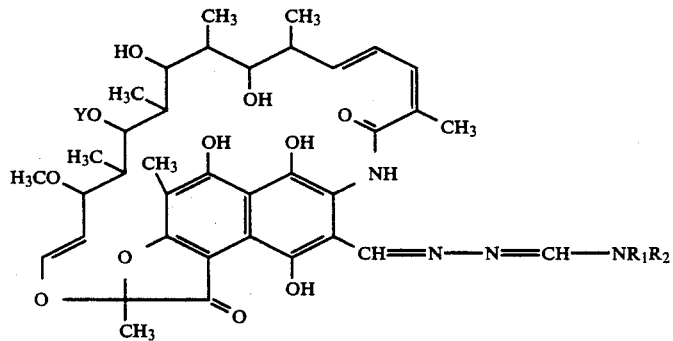

as well as the corresponding oxidized quinones.

Such compounds are provided with strong antibacterial activity against Gram-positive and Gram-negative bacteria and especially against Mycobacterium tuberculosis.

It is known that rifampicin is the basic rifamycin derivative worldwide used against Mycobacterium Tuberculosis.

Many other rifamycin derivatives have been discovered and patented in the past years.

The most promising of the known rifamycin derivatives, including rifampicin, have been studied and compared with each other by Jean M. Dickinson and D.A. Mitchison of the Department of Bacteriology, Royal Postgraduate Medical School of London who have concluded that the 3-(N-piperidinomethylazino)methylrifamycin SV (labelled by the patentees as "FCE 22250") has the most important bactericidal activity and it is the most effective sterilizing drug having also a long half-life. Such results have been published on TUBERCLE (1987) 68, 183-193.

The outstanding biological characteristics including anti-bacterial activity and favourable pharmacokinetic properties of FCE 22250 on laboratory animals are reported in THE JOURNAL OF ANTIBIOTICS, Vol. 38, No. 6, pp. 779-786, June 1985: the laboratory animals were treated by oral route but especially intravenously with the cited drug.

Further accurate tests carried out "in vivo" by oral administration of FCE 22250 have shown that it is absorbed in a not completely satisfactory way, what presently makes it as such unsuitable for practical oral administration: also, at present no salt or ester derivatives of FCE 22250 which may be hydrolized in the organism after absorption are known.

This problem has been taken into very careful consideration and it has been found that the bioavailability and water solubility of FCE 22250 in an environment with a pH from substantially neutral to about 1 (as it is in the gastrointestinal tract of animals) are rather low: this may explain why FC 22250 is unsatisfactorily absorbed when it is administered by oral route.

SUMMARY OF THE INVENTION

It has now been surprisingly discovered that the oxidized (quinone) derivative of FCE 22250, which is the 3-(N-piperidinomethyl-azino)methylrifamycin S (labelled by the patentees as FCE 22807) is provided with a surprisingly high water solubility and enhanced bioavailability with reference to its reduced parent compound (FCE 22250). Thus, FCE 22807 is well suited for oral administration. It is also well known that in the organs of animals (especially in the liver) there are enzymes transforming oxidized compounds into the corresponding reduced compounds and vice-versa. It might so be that FCE 22807 gets wholly or partially metabolized into the parent reduced FCE 22250.

The title compound, 3-(N-piperidinomethylazino)methylrifamycin S (FCE 22807) and its synthesis were already described at the end of Example 1 of the cited U.S. Pat. No. 4,447,432, where such a product was identified by its MS and Rf characteristics.

Nothing however was said or was obvious for one skilled in the art for leaving to understand that the oxidized (quinone) FCE 22807 had a so enhanced solubility and bioavailability with reference to its parent reduced (hydroquinone) FCE 22250.

Indeed the very many works carried out in many Universities and laboratories throughout the world have always made use of the reduced FCE 22250 (see also IL FARMACO, May 1985, No. 5) and never of its parent FCE 22807.

DESCRIPTION OF THE PREFERRED EMBODIMENTS

The really surprising good solubility and bioavailability of FCE 22807 make it possible to prepare pharmaceutical compositions comprising 3-(N-piperidinomethyl-azino)methylrifamycin S as active ingredient, suitable for oral administration. Such a pharmaceutical composition is the object of the present invention. The present invention accordingly provides an orally administrable pharmaceutical composition comprising a pharmaceutically acceptable carrier and/or diluent and, as active substance, 3-(N-piperidinomethyl-azino)methylrifamycin S.

The orally administrable pharmaceutical compositions of the invention comprise 3-(N-piperidinomethyl-azino)methylrifamycin S as active substance in association with a pharmaceutically acceptable excipient (which can be a carrier or diluent). They are suitably presented in solid or liquid form.

The compositions are administered orally in the form of, for example, tablets, capsules, sugar or film coated tablets, liquid solutions or suspensions. The dosage of the active ingredient depends on the age, weight and conditions of the patient, and is chosen to yield the desired activity without causing adverse side-effects. For example, a typical effective dosage for an adult human is in the range of about 0.001 to 0.5 mg/kg per day, preferably from 0.01 to 0.25 mg/kg per day. The compositions of the invention are therefore typically presented in unit dosage form comprising from 10 to 200 mg of active substance.

The oral formulations of the pharmaceutical compositions of the invention are usually prepared following conventional methods and are administered in a pharmaceutically suitable form. The said pharmaceutical preparations may be manufactured in any known manner, for example, by means of mixing, granulating, tabletting, sugar-coating, or film-coating processes.

Solid oral forms may comprise, together with the active ingredient, diluents, e.g., lactose, dextrose, saccharose, cellulose, corn starch or potato starch; lubricants, e.g. silica, talc, stearic acid, magnesium or calcium stearate; and/or polyethylene glycols; binding agents, e.g. starches, arabic gums, gelatin, methyl-cellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations.

The liquid dispersions for oral administration may be e.g. syrups, emulsions and suspensions. Liquid carriers include water, syrup, peanut oil, olive oil and the like.

The syrup may contain as carrier, for example, saccharose or saccharose with glycerine and/or mannitol and/or sorbitol.

The invention further provides the use of 3-(N-piperidinomethyl-azino)methylrifamycin S in the preparation of a medicament suitable for oral administration in the treatment of bacterial infection. Antibacterial activity may be exhibited against Gram-positive and Gram-negative bacteria and against Mycobacterium Tubercolosis.

The different solubility and intrinsic dissolution rate of FCE 22250 and FCE 22807 in aqueous solutions are reported in the following Tables 1 and 2.

TABLE 1

| Solubility at 37° C. (after 3 hours) - mcg/ml (by HPLC method) | | |
|---|---|---|
| | FCE 22807 | FCE 22250 |
| $H_2O$ | 6.3 | 1 |
| pH 1.2 (Chloride buffer)* | 168.4 | 1 |
| pH 3.1 (glycine buffer)* | 16.6 | 1 |
| pH 5.5 (acetate buffer)* | 6.5 | 1 |
| pH 6.8 (phosphate buffer)* | 20.0 | 6.9 |
| pH 7.4 (phosphate buffer)* | 58.8 | 34.0 |

*Ionic strength = 0.1

TABLE 2

| Intrinsic dissolution rate $mg/cm^2/sec.$* | |
|---|---|
| FCE 22807 | FC 2250 |
| $6.592 \times 10^{-5}$ | $3.12 \times 10^{-5}$ | ionic strength = 0.1
*by the Paddle method - U.S.P. XXI
300 r.p.m.; T = 37° C.; pH = 7.4 phosphate buffer Lipophylic properties of FCE 22807 and of FCE 22250 as compared with rifampicin have been also determined by chromatography in reverse phase according to the method disclosed in the literature for the Ansamycin compounds (see: IL FARMACO, Ed. Sc., 28, 298 (1973). The results (lipophylic index, stated as value of chromatographic mobility) which have been obtained are:

Rifampicin = −0.305
FCE 22250 = −0.280
FCE 22807 = −0.325 and show that the lipophylic properties of FCE 22807 are better than those of FCE 22250 and even also of rifampicin.

What is claimed as new and desired to be secured by letters patent of the United States is:

1. A method of treating a patient with a bacterial infection, comprising orally administering an antibacterial effective amount of 3-(N-piperidinomethylazino)-methylrifamycin S to said patient.

* * * * *